United States Patent
Mathewuse

Patent Number: 5,707,341
Date of Patent: Jan. 13, 1998

[54] PENIS GRIPPING DEVICE

[76] Inventor: James L. Mathewuse, 825 Cypress St., C-781, Tarpon Springs, Fla. 34689

[21] Appl. No.: 658,988
[22] Filed: Jun. 4, 1996
[51] Int. Cl.$^6$ ............................................. A61F 5/00
[52] U.S. Cl. ................................................... 600/39
[58] Field of Search ................................. 600/38–41

[56] References Cited

U.S. PATENT DOCUMENTS

| | | | |
|---|---|---|---|
| 2,874,698 | 2/1959 | Sell. | |
| 3,820,533 | 6/1974 | Jones | 128/79 |
| 4,175,554 | 11/1979 | Gerow | 128/79 |
| 4,378,008 | 3/1983 | Osbon, Sr. | 128/79 |
| 4,718,411 | 1/1988 | Stewart | 128/79 |
| 4,856,498 | 8/1989 | Osbon | 128/79 |
| 5,020,522 | 6/1991 | Stewart | 128/79 |
| 5,195,943 | 3/1993 | Chaney | 600/41 |
| 5,234,401 | 8/1993 | Yamanaka | 600/38 |
| 5,243,968 | 9/1993 | Byun | 128/40 |
| 5,244,453 | 9/1993 | Osbon et al. | 600/38 |
| 5,344,396 | 9/1994 | Clark, Jr. | 600/38 |
| 5,421,808 | 6/1995 | Osbon et al. | 600/38 |
| 5,462,514 | 10/1995 | Harris | 600/38 |

*Primary Examiner*—Jennifer Bahr
*Assistant Examiner*—Ryan Carter
*Attorney, Agent, or Firm*—Gene Scott; Patent Law & Venture Group

[57] ABSTRACT

A cylindrical body with a flexible sheath at one end is mountable onto the end of a penis. With a partial vacuum drawn within the body through a one-way valve mounted in the wall of the body, the device is fixed to the penis securely. A weight may be hung from an eyelet of the body for stretching the penis. A plug provides a means for admitting air into the body for removing the device. A cone shaped wrap is secured to the penis in order to prevent the glans-penis from swelling. This wrap provides an air bladder in contact with the glans-penis to counteract swelling when the vacuum is drawn.

6 Claims, 2 Drawing Sheets

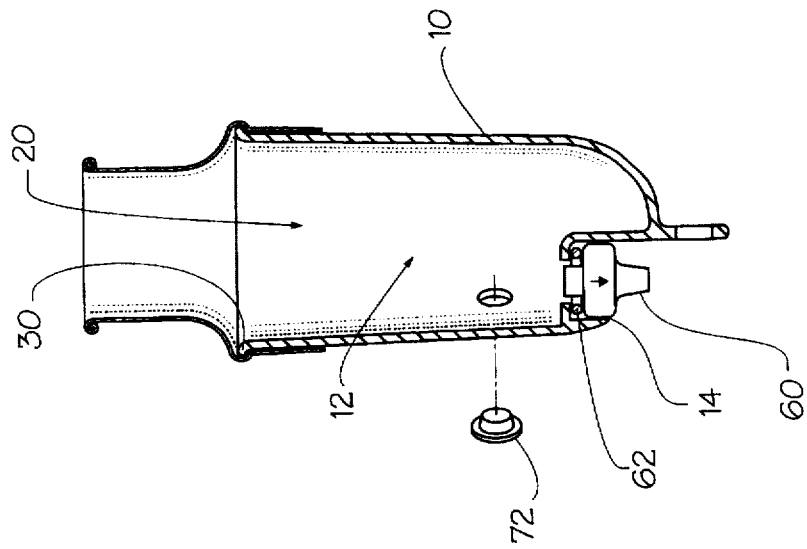
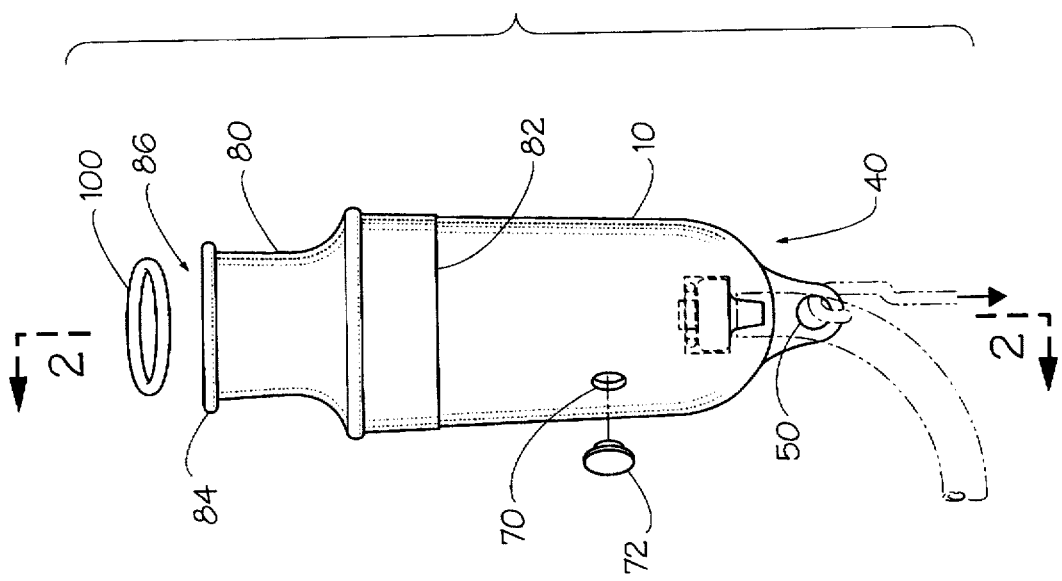

1

PENIS GRIPPING DEVICE

BACKGROUND OF THE INVENTION

1. Field of the Invention

This invention relates generally to devices for gripping or attaching to the human body, and more particularly to a device for gripping the penis without harm thereto.

2. Description of Related Art

Invention and use of devices in the field of the invention is known to the public, as they are used for the intended purposes as defined herein. The following art defines the present state of this art:

Jones, U.S. Pat. No. 3,820,533, describes a device to aid men in attaining and maintaining an erection. The device consists of an inflatable ring to be inserted around the base of the penis and then inflated to apply a radially inward force sufficient to retain blood in the organ; and a tubular sleeve portion with a bulb that can be inserted over the penis and secured about the ring element in sealing. The bulb then can be actuated to develop a low pressure within the interior of the tube and outside the penis, to aid in causing an erection. The ring retaining the blood to maintain the erection, the tubular part then being removable to permit copulation. After copulation, the ring is deflated and removed. The ring can be used in preventing urinary incontinence in males.

Gerow, U.S. Pat. No. 4,175,554 describes a device for receiving and positioning in a simulation of an erection for an impotent male. The device comprises a sleeve-like body enclosed at one end and having the other end open for receiving the penis. After the penis is inserted, a negative pressure is produced in the interior of the body, which has the effect of drawing the penis into the interior of the sleeve in an erection-like position.

Osbon, U.S. Pat. No. 4,378,008 shows a device to assist in the male erection using an evacuation cylinder, having a sealing flange adjacent to a base for carrying an elastic band. A flexible conduit connects to a vacuum source and a valve is closed to hold a partial vacuum in the cylinder, to cause the organ to erect while band is released at just the right time to capture the erection.

Stewart, U.S. Pat. No. 4,718,411 shows a male erecting device that includes an open-ended penile tube adapted to fit over a non-erect penis, which seals against the torso around the base of the organ, and a vacuum pump to produce a vacuum within the tube, the vacuum normally produces an erection in many types of impotence. A specially designed vacuum regulating valve provides an accurate, adjustable limitation on the maximum vacuum which can by used in the penile tube, which is necessary for the safety and well being of the user, to prevent discomfort, pain or damage to the penis. Valves are provided for instantly relieving the vacuum entirely if the user should experience pain or discomfort, for relieving the vacuum automatically after a predetermined time to limit the exposure time of the penis to the vacuum, and to disable the device completely for a further time period after cessation of the vacuum. The entire device is small, compact and self-contained, requiring no connections for pneumatic or electric lines to any equipment remote from the device itself.

Stewart, U.S. Pat. No. 5,020,522 describes a compact vacuum therapy system useful in treating male impotence. The device includes a pump body, which is used for removable mounting on a tube in both storage and operational positions. The pump body includes a reciprocating piston having a circumscribing groove of a width to permit axial shifting of an O-ring sealing during movement of the piston within the pump body. The sealing device then acts as a valve to alternately seal and open a slot defined in the piston transverse to the groove during the strokes of the piston. The piston is axially oriented with the intake and the tube when the pump is mounted to the tube.

Harris, U.S. Pat. No. 5,462,514 describes an apparatus for aiding erection in men comprising an open tubular vacuum cylinder and an mounted electrically powered vacuum generating unit which mounts to an end of the cylinder and supplies a limited vacuum at a relatively high leakage rate and a vacuum controlling valve which may be used to accurately limit the vacuum.

Osbon, U.S. Pat. No. 4,856,498 describes a device for user adaptability including provision for an adapter insert for changing the effective internal diameter of the entry end of a vacuum chamber, an improved constriction means having a generally circular periphery with elongated handle unitary at a single end with an inner torroidal ring, improved vacuum seal connector and a hand pump with an on/off valve for controlling the vacuum.

Chaney, U.S. Pat. No. 5,195,943 shows an elastic constricting ring forming the periphery of a vacuum cylinder into tight surrounding relationship to the base of a penis, by means of a sleeve on the cylinder contiguous with the restricting ring. The sleeve is provided with a camming surface that reacts against a fixed cam element on the cylinder so that when the sleeve is rotated it is cammed axially toward the end of the vacuum cylinder in which case the restricting ring is forced off the cylinder and onto the base of the penis.

Yamanaka, U.S. Pat. No. 5,234,401 shows a device that assists in penis erection. The device contains a sealing device for accommodating a penis inside, the device also has an extracting hose connected to the device, and a pump for extracting air from within the sealing device. An expandable circular bag provided at the opening of the device and an exhaling hose for supplying air extracted by the pump into the circular bag member is used to expand the circular bag member.

Byun, U.S. Pat. No. 5,243,968 shows a massage device for speedily massaging the penis. The vacuum massage has an elongated, cylindrical receptacle having first and second ends, a deformable cone-shaped member detachably coupled to the first end of the receptacle, and having an opening provided at the central region, and a pump mechanism coupled to the second end of the receptacle. The receptacle includes a relief valve for controlling the vacuum.

Osbon et al., U.S. Pat. No. 5,421,808 describes a self-contained, battery-operated, external vacuum generator that includes an electric motor with an eccentric output shaft coupled with a reciprocating diaphragm pump in a common housing with the electric motor and batteries. A housing vacuum port is removable and mounted inline on a reversible coupler, which is received in an open end of a vacuum chamber for housing the user's flaccid penis for vacuum engorgement therapy. The reversible coupler includes a pair of concentric annular extensions for establishing a vacuum seal with the housing vacuum port. A reverse side of the coupler includes an extended coupling nipple for alternate vacuum seal attachment with tubing connected to a manual pump. The vacuum chamber tapers toward the penis introducing end to facilitate the full engorgement of the glans penis. A relative vacuum indicator on the housing permits the user to monitor the degree of negative pressure applied to the penis, which may then be adjusted with a flow control knob, mounted on the housing. The electric motor is a relatively high torque, low energy consumption motor to prevent pump stall.

Osbon et al., U.S. Pat. No. 5,244,453 shows an improved apparatus including a cylindrical vacuum chamber to cover a penis. The vacuum chamber has an open proximal end and a closed distal end. The distal end tapers to provide an integral ramp for expanding a resilient cincture band onto the outside diameter of the vacuum chamber. A vacuum connector fitting forms at the base of the ramp for evacuation of the chamber. Guard flanges help protect the fitting. The proximal end includes a cincture band groove defined about the outside diameter of the chamber, with a plurality of vent holes in the groove, pneumatically interconnecting the exterior of the chamber with its interior. A cincture band expands onto the outside diameter of the chamber and advances to it proximal end initially resides in the cincture band groove, where it covers and seals the plurality of vent holes. Once desired engorgement is achieved, the cincture band advances to the base of the penis, which simultaneously vents negative pressure within the chamber by uncovering of the vent holes. The construction of the cincture band includes a pair or semi-ellipsoidal handles and an enlarged region to be aligned with the urethra of the penis so as to reduce urethra constriction for improved seminal discharge.

The art described above is primarily for the correction of penile impedance. It does not teach a means for connecting weight members to the penis. The prior art also does not teach a means for prevention of the swelling of the glans-penis under vacuum. The present invention fulfills these needs and provides further related advantages as described in the following summary.

SUMMARY OF THE INVENTION

The present invention teaches certain benefits in construction and use which give rise to the objectives described below. A present invention is built around a rigid cylindrical body with a flexible sheath at one end and is mountable onto the end of a penis. With a partial vacuum drawn within the body through a one-way valve mounted in the wall of the body, the device is fixed to the penis securely. A weight may be hung from an eyelet of the body for stretching the penis. A plug provides a means for admitting air into the body for removing the device. A cone shaped wrap is secured to the penis in order to prevent the glans-penis from swelling. This wrap provides an air bladder in contact with the glans-penis to counteract swelling when the vacuum is drawn. Therefore the primary objective of the present invention is to provide a device for positive and fixed attachment to the male sex organ without the possibility of causing harm to the same. Another objective of the invention is to provide such a device that is easily attached and removed from the penis. A further objective of the invention is to provide a means for exposing the penis to a mild vacuum, while preventing the penis from swelling under the influence of the vacuum. Another important objective of the invention is to provide a means for attaching a weight to the device in order to provide a simplified and save way to stretch the penis.

Other features, advantages and objects of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention, a device for firmly gripping a penis. In such drawings:

FIG. 1 is a front elevational view of the preferred embodiment of the present invention;

FIG. 2 is a side elevational cross-sectional view thereof taken along line 2—2 in FIG. 1;

DETAILED DESCRIPTION OF THE PREFERRED EMBODIMENT

Figure 3:
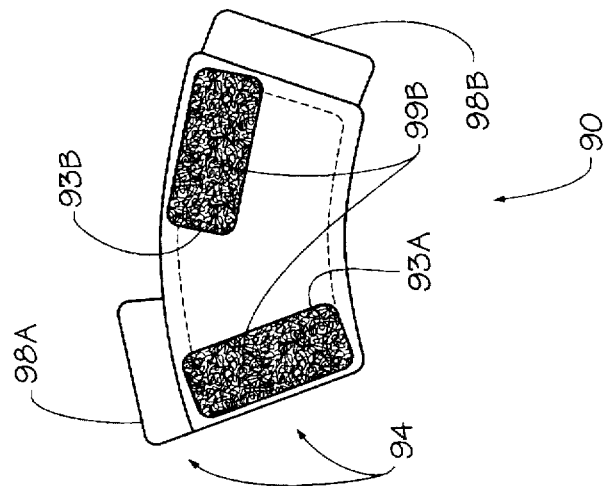
FIG. 3. is the same view as shown in FIG. 2 and further showing the correct manner in which to use the invention with a penis inserted therein, and further the manner in which to use an elastic sheath of the invention.

The above described drawing figures illustrate a device for gripping a penis 4. The device includes, as shown in FIGS. 1 and 2, a rigid, generally cylindrical body 10 having one open end 20 defining an annular rim 30. At the opposing end 40 of the body 10 is a means for attaching a weight 50 to the body, preferably an eye fixed to the body 10, as well as a means for exhausting air 60 from the interior space 12, within the body 10, preferably a one way air valve of any well known type. Such a valve is preferably sealed at a valve aperture 14 in the body 10 by an O-ring 62. The body 10 further includes a means for admitting air 70 into the interior space 12, preferably an aperture in the body stoppered by an aperture plug 72, the plug being removable from the aperture.

A sheath 80 of an elastic, resilient, sheet material has a first open end 82, stretched over the annular rim 30 of the body 10, and thus forms a mechanically secure and air-tight seal with the body 10. The sheath 80 extends coaxially from the body 10 and terminates at a rolled edge 84 defining an entryway 86 into the sheath 80, as well as the body 10. The sheath 80 is preferably hourglass shaped as this shape has proven to be advantageous in providing a superior seal with the shaft 6 of the penis 4.

A means for padded containment 90 of the glans-penis 8, preferably includes an air bladder 92 formed of a flexible and resilient sheet material enclosing, and trapping, a quantity of air within the bladder 92. It has been discovered and found, that the air bladder 92, reacting to the partial vacuum drawn in the internal space 12, tends to swell inwardly, counteracting a tendency of the glans-penis to swell outwardly. Also, preferably, the containment means 90 further includes a means for securing 94 of the bladder in place around the glans-penis 8. The containment means 90 is of such size as to fully enclose the glans-penis 8 of an adult flaccid human penis 4. The penis 4, with the containment means 90, in place, is engagable within the entryway 86 inside the sheath 80 as shown in FIG. 3. The sheath 80 is resilient so as to be able to stretch over the containment means 90 for insertion of the later therein. A partial vacuum within the body 10 biases the sheath 80 into intimate contact with the shaft 6 of the penis 4 and also the containment means 90. It has been found that the partial vacuum tends to swell the glans-penis 8 and also the bladder 92. Since the bladder 92 is restricted within the containment means 90, it cannot swell outwardly, and thus restricts the swelling of the glans-penis 8.

This novel mechanism for prevention of swelling in the glans-penis 8 avoids discomfort normally experienced when the male organ is exposed to a mild vacuum as is the case with the prior art.

Figure 4:
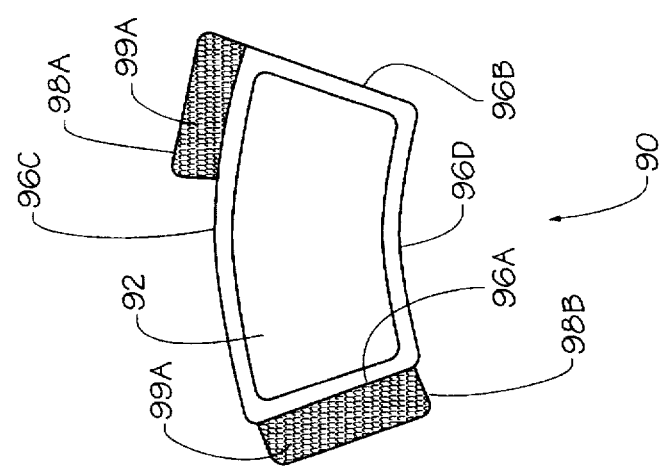
FIG. 4 is a plan view of a front side, laid flat, of the elastic sheath shown in FIG. 3.
Figure 5:
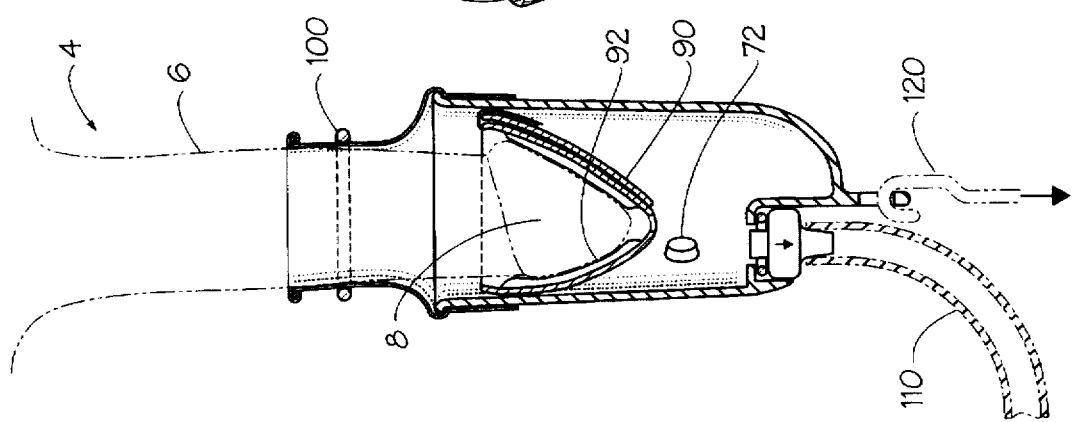
FIG. 5 is a plan view of a reverse side, laid flat, of the elastic sheath shown in FIG. 3.

The containment means 90, when laid flat, as shown in FIGS. 4 and 5, provides two opposing divergent edges 96A, 96B, contiguous with two opposing arcuate edges 96C, 96D, so that the containment means may be rolled into a funnel shape. It should be noticed that along the longer of the arcuate edges 96C a first tab 98A is attached. Also, along one of the divergent edges 96A, a second tab 98B is attached. These tabs 98A, 98B are surfaced (FIG. 4) with a first surface attachment means 99A. Note also, in FIG. 4, the extent of the air bladder 92. On the reverse side of the containment means 90, as shown in FIG. 5, two attachment areas 93A, 93B are shown, each providing a second surface attachment means 99B. The first and second surface attachment means 99A, 99B is preferably Velcro® fastener material, or any other hook and loop type surface fastener material. It is obvious, looking at FIGS. 4 and 5, how the tabs 98A, 98B and attachment areas 93A, 93B are joined as the containment means 90 is rolled with the bladder 92 folded into the interior of the resultant conical, or cone shape.

In use, a male will attach the containment means 90 around his glans-penis 8 and secure it in place with one or both of the tabs 98A, 98B. He will then insert the penis shaft 6 with the containment means 90 in place, into the sheath 80, so that the sheath 80 is secure around the shaft 8. This is best achieved by rolling the rolled edge 84 of the sheath 80 as far as possible toward the rim 30. The sheath 80 may then be stretched to accept the containment means 90. A shaft O-ring 100 may be placed over the sheath 80 and penis 4 to further seal the sheath 80 around the penis shaft 6. With plug 72 inserted into aperture 70, a means for generating a mild vacuum, such as a small vacuum pump (not shown) would then be attached to the valve 60 by, preferably, a flexible tube 110, and a vacuum would be drawn within the interior space 12. With the tube 110 removed from the valve 60, the mild vacuum within the space 12 is maintained since the valve 60 allows air flow only in the direction of the arrow shown in FIGS. 2 and 3. No air can therefore enter the interior space 12 of body 10 and the device is therefore fixed to the penis. A weight 120 may be hung from the weight attaching means 50 as shown in FIG. 3 for the purpose of stretching the penis, or other purposes. When it is desired to remove the device from the penis 4, the plug 72 is removed from aperture 70 thereby admitting air into the interior 12. With pressure balance, the device is simply removed from the penis 4 by reversing the previously described installation steps.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A gripping device comprising:
   a rigid cylindrical body having; a one open end defining an annular rim; a means for attaching a weight to the body; a means for exhausting air from the body; and a means for admitting air into the body;
   a sheath of an elastic, resilient, material having a first open end stretched over the annular rim forming a mechanically secure and air-tight seal therebetween, the sheath extending coaxially from the body and terminating at a rolled edge defining an entryway into the sheath;
   a means for padded containment including an air bladder containing air, the air bladder being formed of a flexible and resilient sheet material and further, including a means for securing the bladder in place on the glans-penis, the air bladder being of such size as to fully enclose the glans-penis of an adult flaccid human penis, including means for securement of the containment means in place on the penis; the penis with the containment means, in place thereon, being engagable within the entryway inside the sheath; whereby a partial vacuum within the body biases the containment means and the penis into intimate contact with the sheath and the body respectively.

2. The device of claim 1 wherein the means for exhausting air from the body is a one way air valve.

3. The device of claim 1 wherein the means for admitting air into the body is an aperture and an aperture plug, the plug being removable from the aperture.

4. The device of claim 1 wherein the means for attaching a weight to the body is a eye fixed to the body in opposition to the one open end.

5. The device of claim 1 wherein the sheet material when laid flat provides two opposing and divergent edges contiguous with two opposing arcuate edges, so that the sheet material may be rolled into a cone shape.

6. The device of claim 1 wherein the sheath is hourglass shaped.

* * * * *